(12) United States Patent
Suzuki et al.

(10) Patent No.: US 9,558,778 B2
(45) Date of Patent: Jan. 31, 2017

(54) LUBRICANT COMPOUND FOR MAGNETIC DISK AND MAGNETIC DISK

(75) Inventors: Kota Suzuki, Tokyo (JP); Koichi Shimokawa, Tokyo (JP); Katsushi Hamakubo, Tokyo (JP); Kae Itoh, Tokyo (JP)

(73) Assignee: WD Media (Singapore) Pte. Ltd., Irvine, CA (US)

( * ) Notice: Subject to any disclaimer, the term of this patent is extended or adjusted under 35 U.S.C. 154(b) by 1133 days.

(21) Appl. No.: 13/260,841

(22) PCT Filed: Mar. 27, 2010

(86) PCT No.: PCT/JP2010/055469
§ 371 (c)(1),
(2), (4) Date: Dec. 13, 2011

(87) PCT Pub. No.: WO2010/116908
PCT Pub. Date: Oct. 14, 2010

(65) Prior Publication Data
US 2012/0127601 A1    May 24, 2012

(30) Foreign Application Priority Data

Mar. 28, 2009   (JP) ................................. 2009-080693

(51) Int. Cl.
*G11B 5/725*    (2006.01)
*C10M 169/04*   (2006.01)
(Continued)

(52) U.S. Cl.
CPC ............ *G11B 5/725* (2013.01); *C10M 169/04* (2013.01); *C07F 9/65812* (2013.01);
(Continued)

(58) Field of Classification Search
None
See application file for complete search history.

(56) References Cited

U.S. PATENT DOCUMENTS

| | | |
|---|---|---|
| 6,013,161 A | 1/2000 | Chen et al. |
| 6,063,248 A | 5/2000 | Bourez et al. |
| | (Continued) | |

FOREIGN PATENT DOCUMENTS

| | | |
|---|---|---|
| JP | 62-066417 | 3/1987 |
| JP | 10-143838 A | 5/1998 |
| | (Continued) | |

OTHER PUBLICATIONS

Solvay Solexis. Fomblin Z Derivatives: Product Data Sheet, 2002.*

*Primary Examiner* — Holly Rickman
*Assistant Examiner* — Lisa Chau
(74) *Attorney, Agent, or Firm* — Sughrue Mion, PLLC

(57) ABSTRACT

A lubricant compound is contained in a lubrication layer of a magnetic disk in which at least a magnetic layer, a protective layer, and a lubrication layer are sequentially provided on a substrate, and the lubricant compound contains a component A represented by Chemical formula 1 and a component B represented by Chemical formula 2:

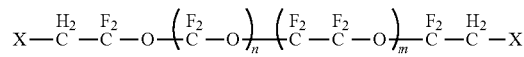

wherein X in Chemical formula 1 represents OH

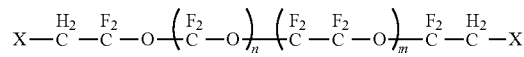

wherein X in Chemical formula 2 represents $OCH_2CH(OH)CH_2OH$, (Continued)

and the lubricant compound further contains a component C made of a specific compound having a phosphezene ring in the structure thereof.

7 Claims, 1 Drawing Sheet

(51) Int. Cl.
C07F 9/6581 (2006.01)
C10M 105/74 (2006.01)
G11B 5/82 (2006.01)

(52) U.S. Cl.
CPC ..... *C10M 105/74* (2013.01); *C10M 2213/043* (2013.01); *C10M 2213/0606* (2013.01); *C10M 2223/08* (2013.01); *C10M 2223/083* (2013.01); *C10N 2230/06* (2013.01); *C10N 2240/204* (2013.01); *C10N 2250/121* (2013.01); *C10N 2280/00* (2013.01); *G11B 5/82* (2013.01)

(56) References Cited

U.S. PATENT DOCUMENTS

| | | |
|---|---|---|
| 6,068,891 A | 5/2000 | O'Dell et al. |
| 6,086,730 A | 7/2000 | Liu et al. |
| 6,099,981 A | 8/2000 | Nishimori |
| 6,103,404 A | 8/2000 | Ross et al. |
| 6,117,499 A | 9/2000 | Wong et al. |
| 6,136,403 A | 10/2000 | Prabhakara et al. |
| 6,143,375 A | 11/2000 | Ross et al. |
| 6,145,849 A | 11/2000 | Bae et al. |
| 6,146,737 A | 11/2000 | Malhotra et al. |
| 6,149,696 A | 11/2000 | Jia |
| 6,150,015 A | 11/2000 | Bertero et al. |
| 6,156,404 A | 12/2000 | Ross et al. |
| 6,159,076 A | 12/2000 | Sun et al. |
| 6,164,118 A | 12/2000 | Suzuki et al. |
| 6,200,441 B1 | 3/2001 | Gornicki et al. |
| 6,204,995 B1 | 3/2001 | Hokkyo et al. |
| 6,206,765 B1 | 3/2001 | Sanders et al. |
| 6,210,819 B1 | 4/2001 | Lal et al. |
| 6,216,709 B1 | 4/2001 | Fung et al. |
| 6,221,119 B1 | 4/2001 | Homola |
| 6,248,395 B1 | 6/2001 | Homola et al. |
| 6,261,681 B1 | 7/2001 | Suekane et al. |
| 6,270,885 B1 | 8/2001 | Hokkyo et al. |
| 6,274,063 B1 | 8/2001 | Li et al. |
| 6,283,838 B1 | 9/2001 | Blake et al. |
| 6,287,429 B1 | 9/2001 | Moroishi et al. |
| 6,290,573 B1 | 9/2001 | Suzuki |
| 6,299,947 B1 | 10/2001 | Suzuki et al. |
| 6,303,217 B1 | 10/2001 | Malhotra et al. |
| 6,309,765 B1 | 10/2001 | Suekane et al. |
| 6,358,636 B1 | 3/2002 | Yang et al. |
| 6,362,452 B1 | 3/2002 | Suzuki et al. |
| 6,363,599 B1 | 4/2002 | Bajorek |
| 6,365,012 B1 | 4/2002 | Sato et al. |
| 6,381,090 B1 | 4/2002 | Suzuki et al. |
| 6,381,092 B1 | 4/2002 | Suzuki |
| 6,387,483 B1 | 5/2002 | Hokkyo et al. |
| 6,391,213 B1 | 5/2002 | Homola |
| 6,395,349 B1 | 5/2002 | Salamon |
| 6,403,919 B1 | 6/2002 | Salamon |
| 6,408,677 B1 | 6/2002 | Suzuki |
| 6,426,157 B1 | 7/2002 | Hokkyo et al. |
| 6,429,984 B1 | 8/2002 | Alex |
| 6,482,330 B1 | 11/2002 | Bajorek |
| 6,482,505 B1 | 11/2002 | Bertero et al. |
| 6,500,567 B1 | 12/2002 | Bertero et al. |
| 6,528,124 B1 | 3/2003 | Nguyen |
| 6,548,821 B1 | 4/2003 | Treves et al. |
| 6,552,871 B2 | 4/2003 | Suzuki et al. |
| 6,565,719 B1 | 5/2003 | Lairson et al. |
| 6,566,674 B1 | 5/2003 | Treves et al. |
| 6,571,806 B2 | 6/2003 | Rosano et al. |
| 6,628,466 B2 | 9/2003 | Alex |
| 6,664,503 B1 | 12/2003 | Hsieh et al. |
| 6,670,055 B2 | 12/2003 | Tomiyasu et al. |
| 6,682,807 B2 | 1/2004 | Lairson et al. |
| 6,683,754 B2 | 1/2004 | Suzuki et al. |
| 6,730,420 B1 | 5/2004 | Bertero et al. |
| 6,743,528 B2 | 6/2004 | Suekane et al. |
| 6,759,138 B2 | 7/2004 | Tomiyasu et al. |
| 6,778,353 B1 | 8/2004 | Harper |
| 6,795,274 B1 | 9/2004 | Hsieh et al. |
| 6,855,232 B2 | 2/2005 | Jairson et al. |
| 6,857,937 B2 | 2/2005 | Bajorek |
| 6,893,748 B2 | 5/2005 | Bertero et al. |
| 6,899,959 B2 | 5/2005 | Bertero et al. |
| 6,916,558 B2 | 7/2005 | Umezawa et al. |
| 6,939,120 B1 | 9/2005 | Harper |
| 6,946,191 B2 | 9/2005 | Morikawa et al. |
| 6,967,798 B2 | 11/2005 | Homola et al. |
| 6,972,135 B2 | 12/2005 | Homola |
| 7,004,827 B1 | 2/2006 | Suzuki et al. |
| 7,006,323 B1 | 2/2006 | Suzuki |
| 7,016,154 B2 | 3/2006 | Nishihira |
| 7,019,924 B2 | 3/2006 | McNeil et al. |
| 7,045,215 B2 | 5/2006 | Shimokawa |
| 7,070,870 B2 | 7/2006 | Bertero et al. |
| 7,090,934 B2 | 8/2006 | Hokkyo et al. |
| 7,099,112 B1 | 8/2006 | Harper |
| 7,105,241 B2 | 9/2006 | Shimokawa et al. |
| 7,119,990 B2 | 10/2006 | Bajorek et al. |
| 7,147,790 B2 | 12/2006 | Wachenschwanz et al. |
| 7,161,753 B2 | 1/2007 | Wachenschwanz et al. |
| 7,166,319 B2 | 1/2007 | Ishiyama |
| 7,166,374 B2 | 1/2007 | Suekane et al. |
| 7,169,487 B2 | 1/2007 | Kawai et al. |
| 7,174,775 B2 | 2/2007 | Ishiyama |
| 7,179,549 B2 | 2/2007 | Malhotra et al. |
| 7,184,139 B2 | 2/2007 | Treves et al. |
| 7,196,860 B2 | 3/2007 | Alex |
| 7,199,977 B2 | 4/2007 | Suzuki et al. |
| 7,208,236 B2 | 4/2007 | Morikawa et al. |
| 7,220,500 B1 | 5/2007 | Tomiyasu et al. |
| 7,229,266 B2 | 6/2007 | Harper |
| 7,239,970 B2 | 7/2007 | Treves et al. |
| 7,252,897 B2 | 8/2007 | Shimokawa et al. |
| 7,277,254 B2 | 10/2007 | Shimokawa et al. |
| 7,281,920 B2 | 10/2007 | Homola et al. |
| 7,292,329 B2 | 11/2007 | Treves et al. |
| 7,301,726 B1 | 11/2007 | Suzuki |
| 7,302,148 B2 | 11/2007 | Treves et al. |
| 7,305,119 B2 | 12/2007 | Treves et al. |
| 7,314,404 B2 | 1/2008 | Singh et al. |
| 7,320,584 B1 | 1/2008 | Harper et al. |
| 7,329,114 B2 | 2/2008 | Harper et al. |
| 7,375,362 B2 | 5/2008 | Treves et al. |
| 7,420,886 B2 | 9/2008 | Tomiyasu et al. |
| 7,425,719 B2 | 9/2008 | Treves et al. |
| 7,471,484 B2 | 12/2008 | Wachenschwanz et al. |
| 7,498,062 B2 | 3/2009 | Calcaterra et al. |
| 7,531,485 B2 | 5/2009 | Hara et al. |
| 7,537,846 B2 | 5/2009 | Ishiyama et al. |
| 7,549,209 B2 | 6/2009 | Wachenschwanz et al. |
| 7,569,490 B2 | 8/2009 | Staud |
| 7,597,792 B2 | 10/2009 | Homola et al. |
| 7,597,973 B2 | 10/2009 | Ishiyama |
| 7,608,193 B2 | 10/2009 | Wachenschwanz et al. |
| 7,632,087 B2 | 12/2009 | Homola |
| 7,656,615 B2 | 2/2010 | Wachenschwanz et al. |
| 7,682,546 B2 | 3/2010 | Harper |
| 7,684,152 B2 | 3/2010 | Suzuki et al. |
| 7,686,606 B2 | 3/2010 | Harper et al. |
| 7,686,991 B2 | 3/2010 | Harper |
| 7,695,833 B2 | 4/2010 | Ishiyama |
| 7,722,968 B2 | 5/2010 | Ishiyama |
| 7,733,605 B2 | 6/2010 | Suzuki et al. |
| 7,736,768 B2 | 6/2010 | Ishiyama |
| 7,755,861 B1 | 7/2010 | Li et al. |
| 7,758,732 B1 | 7/2010 | Calcaterra et al. |
| 7,833,639 B2 | 11/2010 | Sonobe et al. |

(56) References Cited

U.S. PATENT DOCUMENTS

| | | |
|---|---|---|
| 7,833,641 B2 | 11/2010 | Tomiyasu et al. |
| 7,910,159 B2 | 3/2011 | Jung |
| 7,911,736 B2 | 3/2011 | Bajorek |
| 7,924,519 B2 | 4/2011 | Lambert |
| 7,944,165 B1 | 5/2011 | O'Dell |
| 7,944,643 B1 | 5/2011 | Jiang et al. |
| 7,955,723 B2 | 6/2011 | Umezawa et al. |
| 7,983,003 B2 | 7/2011 | Sonobe et al. |
| 7,993,497 B2 | 8/2011 | Moroishi et al. |
| 7,993,765 B2 | 8/2011 | Kim et al. |
| 7,998,912 B2 | 8/2011 | Chen et al. |
| 8,002,901 B1 | 8/2011 | Chen et al. |
| 8,003,237 B2 | 8/2011 | Sonobe et al. |
| 8,012,920 B2 | 9/2011 | Shimokawa |
| 8,038,863 B2 | 10/2011 | Homola |
| 8,057,926 B2 | 11/2011 | Ayama et al. |
| 8,062,778 B2 | 11/2011 | Suzuki et al. |
| 8,064,156 B1 | 11/2011 | Suzuki et al. |
| 8,076,013 B2 | 12/2011 | Sonobe et al. |
| 8,092,931 B2 | 1/2012 | Ishiyama et al. |
| 8,100,685 B1 | 1/2012 | Harper et al. |
| 8,101,054 B2 | 1/2012 | Chen et al. |
| 8,125,723 B1 | 2/2012 | Nichols et al. |
| 8,125,724 B1 | 2/2012 | Nichols et al. |
| 8,137,517 B1 | 3/2012 | Bourez |
| 8,142,916 B2 | 3/2012 | Umezawa et al. |
| 8,163,093 B1 | 4/2012 | Chen et al. |
| 8,171,949 B1 | 5/2012 | Lund et al. |
| 8,173,282 B1 | 5/2012 | Sun et al. |
| 8,178,480 B2 | 5/2012 | Hamakubo et al. |
| 8,206,789 B2 | 6/2012 | Suzuki |
| 8,218,260 B2 | 7/2012 | Iamratanakul et al. |
| 8,247,095 B2 | 8/2012 | Champion et al. |
| 8,257,783 B2 | 9/2012 | Suzuki et al. |
| 8,298,609 B1 | 10/2012 | Liew et al. |
| 8,298,689 B2 | 10/2012 | Sonobe et al. |
| 8,309,239 B2 | 11/2012 | Umezawa et al. |
| 8,316,668 B1 | 11/2012 | Chan et al. |
| 8,331,056 B2 | 12/2012 | O'Dell |
| 8,354,618 B1 | 1/2013 | Chen et al. |
| 8,367,228 B2 | 2/2013 | Sonobe et al. |
| 8,383,209 B2 | 2/2013 | Ayama |
| 8,394,243 B1 | 3/2013 | Jung et al. |
| 8,397,751 B1 | 3/2013 | Chan et al. |
| 8,399,809 B1 | 3/2013 | Bourez |
| 8,402,638 B1 | 3/2013 | Treves et al. |
| 8,404,056 B1 | 3/2013 | Chen et al. |
| 8,404,369 B2 | 3/2013 | Ruffini et al. |
| 8,404,370 B2 | 3/2013 | Sato et al. |
| 8,406,918 B2 | 3/2013 | Tan et al. |
| 8,414,966 B2 | 4/2013 | Yasumori et al. |
| 8,425,975 B2 | 4/2013 | Ishiyama |
| 8,431,257 B2 | 4/2013 | Kim et al. |
| 8,431,258 B2 | 4/2013 | Onoue et al. |
| 8,453,315 B2 | 6/2013 | Kajiwara et al. |
| 8,488,276 B1 | 7/2013 | Jung et al. |
| 8,491,800 B1 | 7/2013 | Dorsey |
| 8,492,009 B1 | 7/2013 | Homola et al. |
| 8,492,011 B2 | 7/2013 | Itoh et al. |
| 8,496,466 B1 | 7/2013 | Treves et al. |
| 8,517,364 B1 | 8/2013 | Crumley et al. |
| 8,517,657 B2 | 8/2013 | Chen et al. |
| 8,524,052 B1 | 9/2013 | Tan et al. |
| 8,530,065 B1 | 9/2013 | Chernyshov et al. |
| 8,546,000 B2 | 10/2013 | Umezawa |
| 8,551,253 B2 | 10/2013 | Na'Im et al. |
| 8,551,627 B2 | 10/2013 | Shimada et al. |
| 8,556,566 B2 | 10/2013 | Suzuki et al. |
| 8,559,131 B2 | 10/2013 | Masuda et al. |
| 8,562,748 B1 | 10/2013 | Chen et al. |
| 8,565,050 B1 | 10/2013 | Bertero et al. |
| 8,570,844 B1 | 10/2013 | Yuan et al. |
| 8,580,410 B2 | 11/2013 | Onoue |
| 8,584,687 B1 | 11/2013 | Chen et al. |
| 8,591,709 B1 | 11/2013 | Lim et al. |
| 8,592,061 B2 | 11/2013 | Onoue et al. |
| 8,596,287 B1 | 12/2013 | Chen et al. |
| 8,597,723 B1 | 12/2013 | Jung et al. |
| 8,603,649 B2 | 12/2013 | Onoue |
| 8,603,650 B2 | 12/2013 | Sonobe et al. |
| 8,605,388 B2 | 12/2013 | Yasumori et al. |
| 8,605,555 B1 | 12/2013 | Chernyshov et al. |
| 8,608,147 B1 | 12/2013 | Yap et al. |
| 8,609,263 B1 | 12/2013 | Chernyshov et al. |
| 8,619,381 B2 | 12/2013 | Moser et al. |
| 8,623,528 B2 | 1/2014 | Umezawa et al. |
| 8,623,529 B2 | 1/2014 | Suzuki |
| 8,634,155 B2 | 1/2014 | Yasumori et al. |
| 8,658,003 B1 | 2/2014 | Bourez |
| 8,658,292 B1 | 2/2014 | Mallary et al. |
| 8,665,541 B2 | 3/2014 | Saito |
| 8,668,953 B1 | 3/2014 | Buechel-Rimmel |
| 8,674,327 B1 | 3/2014 | Poon et al. |
| 8,685,214 B1 | 4/2014 | Moh et al. |
| 8,696,404 B2 | 4/2014 | Sun et al. |
| 8,711,499 B1 | 4/2014 | Desai et al. |
| 8,743,666 B1 | 6/2014 | Bertero et al. |
| 8,758,912 B2 | 6/2014 | Srinivasan et al. |
| 8,787,124 B1 | 7/2014 | Chernyshov et al. |
| 8,787,130 B1 | 7/2014 | Yuan et al. |
| 8,791,391 B2 | 7/2014 | Bourez |
| 8,795,765 B2 | 8/2014 | Koike et al. |
| 8,795,790 B2 | 8/2014 | Sonobe et al. |
| 8,795,857 B2 | 8/2014 | Ayama et al. |
| 2002/0060883 A1 | 5/2002 | Suzuki |
| 2003/0022024 A1 | 1/2003 | Wachenschwanz |
| 2004/0022387 A1 | 2/2004 | Weikle |
| 2004/0072034 A1 | 4/2004 | Shimokawa et al. |
| 2004/0132301 A1 | 7/2004 | Harper et al. |
| 2004/0202793 A1 | 10/2004 | Harper et al. |
| 2004/0202865 A1 | 10/2004 | Homola et al. |
| 2004/0209123 A1 | 10/2004 | Bajorek et al. |
| 2004/0209470 A1 | 10/2004 | Bajorek |
| 2005/0036223 A1 | 2/2005 | Wachenschwanz et al. |
| 2005/0142990 A1 | 6/2005 | Homola |
| 2005/0150862 A1 | 7/2005 | Harper et al. |
| 2005/0151282 A1 | 7/2005 | Harper et al. |
| 2005/0151283 A1 | 7/2005 | Bajorek et al. |
| 2005/0151300 A1 | 7/2005 | Harper et al. |
| 2005/0155554 A1 | 7/2005 | Saito |
| 2005/0167867 A1 | 8/2005 | Bajorek et al. |
| 2005/0217353 A1* | 10/2005 | Ishiyama .................. 73/104 |
| 2005/0263401 A1 | 12/2005 | Olsen et al. |
| 2005/0282045 A1* | 12/2005 | Sonoda .................. 428/843.5 |
| 2006/0147758 A1 | 7/2006 | Jung et al. |
| 2006/0181697 A1 | 8/2006 | Treves et al. |
| 2006/0207890 A1 | 9/2006 | Staud |
| 2007/0070549 A1 | 3/2007 | Suzuki et al. |
| 2007/0245909 A1 | 10/2007 | Homola |
| 2008/0075845 A1 | 3/2008 | Sonobe et al. |
| 2008/0093760 A1 | 4/2008 | Harper et al. |
| 2009/0023017 A1 | 1/2009 | Tomiyasu et al. |
| 2009/0117408 A1 | 5/2009 | Umezawa et al. |
| 2009/0136784 A1 | 5/2009 | Suzuki et al. |
| 2009/0169922 A1 | 7/2009 | Ishiyama |
| 2009/0191331 A1 | 7/2009 | Umezawa et al. |
| 2009/0202866 A1 | 8/2009 | Kim et al. |
| 2009/0311557 A1 | 12/2009 | Onoue et al. |
| 2010/0028721 A1* | 2/2010 | Hamakubo et al. .......... 428/848 |
| 2010/0143752 A1 | 6/2010 | Ishibashi et al. |
| 2010/0190035 A1 | 7/2010 | Sonobe et al. |
| 2010/0196619 A1 | 8/2010 | Ishiyama |
| 2010/0196740 A1 | 8/2010 | Ayama et al. |
| 2010/0209601 A1 | 8/2010 | Shimokawa et al. |
| 2010/0215992 A1 | 8/2010 | Horikawa et al. |
| 2010/0232065 A1 | 9/2010 | Suzuki et al. |
| 2010/0247965 A1 | 9/2010 | Onoue |
| 2010/0261039 A1 | 10/2010 | Itoh et al. |
| 2010/0279151 A1 | 11/2010 | Sakamoto et al. |
| 2010/0300884 A1 | 12/2010 | Homola et al. |
| 2010/0304186 A1 | 12/2010 | Shimokawa |
| 2011/0097603 A1 | 4/2011 | Onoue |
| 2011/0097604 A1 | 4/2011 | Onoue |
| 2011/0171495 A1 | 7/2011 | Tachibana et al. |

(56) References Cited

U.S. PATENT DOCUMENTS

| | | |
|---|---|---|
| 2011/0206947 A1 | 8/2011 | Tachibana et al. |
| 2011/0212346 A1 | 9/2011 | Onoue et al. |
| 2011/0223446 A1 | 9/2011 | Onoue et al. |
| 2011/0244119 A1 | 10/2011 | Umezawa et al. |
| 2011/0299194 A1 | 12/2011 | Aniya et al. |
| 2011/0311841 A1 | 12/2011 | Saito et al. |
| 2012/0069466 A1 | 3/2012 | Okamoto et al. |
| 2012/0070692 A1 | 3/2012 | Sato et al. |
| 2012/0077060 A1 | 3/2012 | Ozawa |
| 2012/0127599 A1 | 5/2012 | Shimokawa et al. |
| 2012/0127601 A1 | 5/2012 | Suzuki et al. |
| 2012/0129009 A1 | 5/2012 | Sato et al. |
| 2012/0140359 A1 | 6/2012 | Tachibana |
| 2012/0141833 A1 | 6/2012 | Umezawa et al. |
| 2012/0141835 A1 | 6/2012 | Sakamoto |
| 2012/0148875 A1 | 6/2012 | Hamakubo et al. |
| 2012/0156523 A1 | 6/2012 | Seki et al. |
| 2012/0164488 A1 | 6/2012 | Shin et al. |
| 2012/0170152 A1 | 7/2012 | Sonobe et al. |
| 2012/0171369 A1 | 7/2012 | Koike et al. |
| 2012/0175243 A1 | 7/2012 | Fukuura et al. |
| 2012/0189872 A1 | 7/2012 | Umezawa et al. |
| 2012/0196049 A1 | 8/2012 | Azuma et al. |
| 2012/0207919 A1 | 8/2012 | Sakamoto et al. |
| 2012/0225217 A1 | 9/2012 | Itoh et al. |
| 2012/0251842 A1 | 10/2012 | Yuan et al. |
| 2012/0251846 A1 | 10/2012 | Desai et al. |
| 2012/0276417 A1 | 11/2012 | Shimokawa et al. |
| 2012/0308722 A1 | 12/2012 | Suzuki et al. |
| 2013/0040167 A1 | 2/2013 | Alagarsamy et al. |
| 2013/0071694 A1 | 3/2013 | Srinivasan et al. |
| 2013/0165029 A1 | 6/2013 | Sun et al. |
| 2013/0175252 A1 | 7/2013 | Bourez |
| 2013/0216865 A1 | 8/2013 | Yasumori et al. |
| 2013/0230647 A1 | 9/2013 | Onoue et al. |
| 2013/0314815 A1 | 11/2013 | Yuan et al. |
| 2014/0011054 A1 | 1/2014 | Suzuki |
| 2014/0044992 A1 | 2/2014 | Onoue |
| 2014/0050843 A1 | 2/2014 | Yi et al. |
| 2014/0151360 A1 | 6/2014 | Gregory et al. |

FOREIGN PATENT DOCUMENTS

| | | | |
|---|---|---|---|
| JP | 10143838 A | * | 5/1998 |
| JP | 2001-052327 A | | 2/2001 |
| JP | 2002-294266 A | | 10/2002 |
| JP | 2002293787 A | * | 10/2002 |
| JP | 2004-152460 A | | 5/2004 |
| JP | 2006-012215 A | | 1/2006 |
| JP | 2007-193924 A | | 8/2007 |
| JP | 2010-108583 A | | 5/2010 |
| WO | 2008/038799 A1 | | 4/2008 |
| WO | WO 2008038799 A1 | * | 4/2008 |

* cited by examiner

LUBRICANT COMPOUND FOR MAGNETIC DISK AND MAGNETIC DISK

CROSS REFERENCE TO RELATED APPLICATION

This application is a National Stage of International Application No. PCT/JP2010/55469 filed Mar. 27, 2010, claiming priority based on Japanese Patent Application No. 2009-080693, filed Mar. 28, 2009, the contents of all of which (including chemical formulas) are incorporated herein by reference in their entirety.

TECHNICAL FIELD

The present invention relates to a magnetic disk to be mounted on a magnetic disk device such as a hard-disk drive (hereinafter abbreviated as HDD) and a lubricant compound for a magnetic disk.

BACKGROUND ART

With the recent trend to higher-capacity information processing, various information recording technologies have been developed. Particularly, a surface recording density of an HDD using the magnetic recording technology has continuously increased by the rate of approximately 100% a year. In recent years, an information recording capacity exceeding 250 GB per disk is required for a magnetic disk having a diameter of 2.5 inches used in HDD or the like, and in order to meet such demand, realization of an information recording density exceeding 400 Gbits per 1 square inch is in demand. In order to achieve the high recording density in a magnetic disk used in an HDD or the like, magnetic crystal grains constituting a magnetic recording layer handling recording of an information signal need to be refined, and its layer thickness needs to be reduced at the same time. However, in the case of a magnetic disk of an in-plane magnetic recording method (also referred to as longitudinal magnetic recording method or horizontal magnetic recording method) which has been merchandized, as the result of development of the refining of the magnetic crystal grains, a thermal fluctuation phenomenon in which thermal stability of the recording signal is damaged by a superparamagnetic phenomenon and the recording signal is lost begins to occur, which makes an obstructive factor to higher recording density of a magnetic disk.

In order to solve this obstructive factor, a magnetic recording medium for a perpendicular magnetic recording method has been proposed recently. In the case of the perpendicular magnetic recording method, unlike the in-plane magnetic recording method, a magnetization easy axis of a magnetic recording layer is adjusted to be oriented in the perpendicular direction with respect to a substrate surface. As compared with the in-plane recording method, the perpendicular magnetic recording method can suppress the thermal fluctuation phenomenon, and is suitable for higher recording density. This type of perpendicular magnetic recording mediums include a so-called two-layer type perpendicular magnetic recording disk provided with a soft magnetic underlayer made of a soft magnetic body on a substrate and a perpendicular magnetic recording layer made of a hard magnetic body as described in Japanese Unexamined Patent Application Publication No. 2002-74648, for example.

In a prior-art magnetic disk, a protective layer and a lubrication layer are provided on a magnetic recording layer formed on a substrate in order to ensure durability and reliability of the magnetic disk. Particularly, the lubrication layer used on the outermost surface requires various characteristics such as long-term stability, chemical substance resistance, friction property, heat resistant property and the like.

In order to accommodate such request, a perfluoropolyether lubricant having a hydroxyl group in the molecule has been widely used as a lubricant for a magnetic disk. For example, as in Japanese Unexamined Patent Application Publication No. S62-66417 (Patent Document 1), a magnetic recording medium in which a perfluoroalkylpolyether lubricant having a structure of $HOCH_2CF_2O(C_2F_4O)_p(CF_2O)_q CF_2CH_2OH$ having a hydroxyl group at both ends of the molecule is applied is well known. If there is a hydroxyl group in a molecule of a lubricant, it is known that an adhesion characteristic of the lubricant to the protective layer can be obtained by means of an interaction between the protective layer and the hydroxyl group.

CITATION LIST

Patent Literature

Patent Document 1: Japanese Unexamined Patent Application Publication No. S62-66417

SUMMARY OF INVENTION

Technical Problem

As described above, the information recording density of 400 Gbit/inch$^2$ or more has been required for the recent HDD, but in order to effectively use a limited disk area, an LUL (Load Unload) type HDD has begun to be used instead of the prior-art CSS (Contact Start and Stop) method in a start/stop mechanism of the HDD. In the LUL method, when an HDD is stopped, a magnetic head is retreated onto an inclined base called a ramp located outside the magnetic disk and in a start operation, after the magnetic disk starts rotating, the magnetic head is made to slide from the ramp onto the magnetic disk, floated and flown for recording and reproducing. In a stop operation, the magnetic head is retreated to the ramp outside the magnetic disk and then, the rotation of the magnetic disk is stopped. This series of operations are called LUL operations. In a magnetic disk to be mounted on the LUL-method HDD, a contact sliding region (CSS region) with the magnetic head as in the CSS method does not have to be provided, and thus, a recording and reproducing area can be expanded, which is preferable for a higher information capacity.

In order to improve the information recording density under these circumstances, a spacing loss needs to be reduced as much as possible by reducing a floating amount of the magnetic head. In order to achieve the information recording density of 400 Gbits or more per 1 square inch, the floating amount of the magnetic head needs to be at least 5 nm or less. In the LUL method, unlike the CSS method, a projection and recess shape for the CSS does not have to be provided on the magnetic disk surface, whereby the magnetic disk surface can be made extremely smooth. Thus, in the magnetic disk to be mounted on the LUL method HDD, the magnetic-head floating amount can be further lowered as compared with the CSS method, whereby a higher S/N ratio of the recording signal can be realized, and contribution can be made to a higher recording capacity of a magnetic disk device, which is an advantage.

Due to the further decrease of the magnetic-head floating amount promoted by recent introduction of the LUL method, a stable operation of the magnetic disk even with a low floating amount not more than 5 nm is in demand at the present. Particularly, as described above, the recording method of the magnetic disk has been changing from the in-plane magnetic recording method to the perpendicular magnetic recording method, and an increase in the capacity of a magnetic disk and a decrease in a flying height in compliance with that are in strong demand.

Also, in recent years, the magnetic disk devices are widely used not only as a storage device of a conventional personal computer but in mobile applications including a mobile phone, a car-navigation system and the like, and due to diversification of the applications, environmental resistances required for the magnetic disk has been extremely severe. Therefore, in view of these situations, further improvement of durability of the magnetic disk or durability of a lubricant constituting a lubrication layer is more imminent than ever.

Also, with the recent rapid improvement of the information recording density of the magnetic disk, further reduction of a magnetic spacing between the magnetic head and the recording layers of the magnetic disk is in demand in addition to the decrease of the floating amount of the magnetic head, and a lubrication layer located between the magnetic head and the recording layer of the magnetic disk needs to be further thinned. A lubricant used for the lubrication layer on the outermost surface of the magnetic disk has a large influence on durability of the magnetic disk, but even if it is made into a thin film, stability and reliability are indispensable for the magnetic disk.

Hitherto, since favorable adhesion properties of the lubricant to the protective layer can be obtained by the interaction between a carbon protective layer and the hydroxyl group in the lubricant molecule due to presence of a polar group such as the hydroxyl group in the molecule of the lubricant, particularly a perfluoropolyether lubricant having a hydroxyl group at both ends of the molecule has been favorably used.

Particularly, in magnetic disks for mobile applications, FOMBLIN Z-TETRAOL (product name) by Solvay Solexis, Inc., which is a perfluoropolyether lubricant, has been widely used as the lubricant, for example. As this lubricant, those refined by various refining methods including supercritical extraction, distillation and the like are used in many cases. It is known by examination by the inventor that this FOMBLIN Z-TETRAOL (product name) lubricant contains a component having various terminal groups.

A bis-form component expressed as follows:

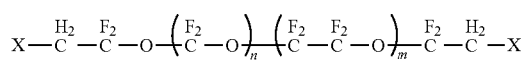

(hereinafter referred to as a component D), which is one of such terminal groups, binds with (is adsorbed by) a protective film particularly strongly, and thus, it works to reduce abrasion of the protective film or physical damage on the magnetic recording medium during LUL or in head contact. However, on the other hand, since the component D is contained, it has a defect that problems such as aggregation of the lubricant and pickup of the lubricant (a phenomenon in which the lubricant transfers to the head side) can easily occur. The lubricant pickup is considered to be caused by contact of the head with the lubricant which has increased its thickness by aggregation. Reduction of the aggregation of the lubricant, the lubricant pickup or physical damage on the magnetic recording medium is an important and imminent problem to be solved in realizing a narrower head clearance in the future.

Recently, in the magnetic head, reduction of spacing has rapidly progressed due to introduction of the Dynamic Flying Height (DFH) technology in which a magnetic pole distal end portion is thermally expanded by generating heat through energization of a thin-film resistance body provided inside an element, and development of a medium which satisfies a back-off margin of a DFH element at 2 nm or less is needed. As described above, realization of a magnetic disk having high reliability is in demand under the circumstances of lower floating amount of the magnetic head and reduction of the magnetic spacing involved with the recent higher recording density.

The present invention was made in view of the above-described prior-art problems and has an object to provide a magnetic disk that can realize further reduction of the magnetic spacing and moreover, has high reliability under the lower floating amount of the magnetic head involved with the recent rapid increase in the recording density and extremely severe environmental resistance involved with diversification of the applications and a lubricant compound for a magnetic disk used for the lubrication layer of the magnetic disk.

Solution to Problem

The inventor has found that the above-described problems can be solved by the following invention as the result of keen examination and completed the present invention.

That is, the present invention has the following configuration:

(Composition 1)

A lubricant compound for a magnetic disk characterized in that the lubricant compound contained in a lubrication layer of a magnetic disk in which at least a magnetic layer, a protective layer, and the lubrication layer are sequentially provided on a substrate, in which the lubricant compound contains a component A represented by Chemical formula 1 and a component B represented by Chemical formula 2:

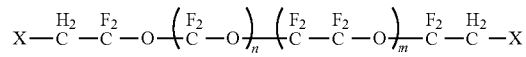

wherein X in Chemical formula 1 represents OH

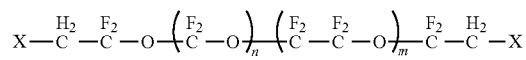

wherein X in Chemical formula 2 represents $OCH_2CH(OH)CH_2OH$, and the lubricant compound further contains at least one type of a component C, wherein the component C is selected from compounds C-1, C-2 and C-3 represented by the following formulae:

(C-1)

-continued (C-2)

$$HO\diagdown\diagup\diagdown_O\diagdown(Rf)-PN-(Rf)\diagdown_O\diagup\diagdown_{OH}^{OH}$$
$$HO$$

(C-3)

$$HOCH_2CF_2(Rf)OCF_2CH_2OCH_2CHCH_2O—*$$
$$\underset{OH}{|}$$
$$*—CH_2CHCH_2OCH_2CHCH_2OCH_2CF_2(Rf)OCF_2CH_2OH$$
$$\underset{OH}{|}\quad\underset{OH}{|}$$

wherein Rf represents —$(OC_2F_4)m(OCF_2)n$-, and m and n each represents an integer of not less than 1, and PN is represented from one of the following formulae:

$$\begin{array}{c}\text{N}^{\text{P}}\diagdown\text{N}\\\|\quad\|\\\text{P}\diagdown_{\text{N}}\diagup\text{P}\end{array}\!\!\left(-O-\!\!\bigcirc\!\!-CF_3\right)_x$$

$$\begin{array}{c}\text{N}^{\text{P}}\diagdown\text{N}\\\|\quad\|\\\text{P}\diagdown_{\text{N}}\diagup\text{P}\end{array}\!(OCH_2CF_3)_y$$

wherein x and y each is an integer of 5 when C is compound (C-1) and an integer of 4 when C is compound (C-2).

(Composition 2)

The lubricant compound for a magnetic disk described in the composition 1, characterized in that in the lubricant compound, the ratio of the component C among the component A, the component B, and the component C is 5 to 20 weight %.

(Composition 3)

The magnetic disk, characterized in that at least a magnetic layer, a protective layer, and a lubrication layer are sequentially provided on a substrate, in which the lubrication layer contains the lubricant compound described in the composition 1 or 2.

(Composition 4)

The magnetic disk described in the composition 3, characterized in that the protective layer is a carbon protective layer formed by a plasma CVD method.

(Composition 5)

The magnetic disk described in the composition 3 or 4, characterized in that the magnetic disk is a magnetic disk mounted on a magnetic disk device whose start/stop mechanism is of a load-unload type and used under the head floating amount of 5 nm or less.

Advantages of the Invention

According to the present invention, a lubricant compound for a magnetic disk which can realize further reduction of the magnetic spacing and moreover, in which drawbacks such as the lubricant aggregation, pickup or the like does not occur, and has high reliability under a low floating amount of a magnetic head involved with the recent rapid increase in the recording density and under extremely severe environmental resistance involved with diversification of the applications, and a magnetic disk provided with the lubrication layer containing the lubricant compound can be provided.

BEST MODE FOR CARRYING OUT THE INVENTION

Figure 1:
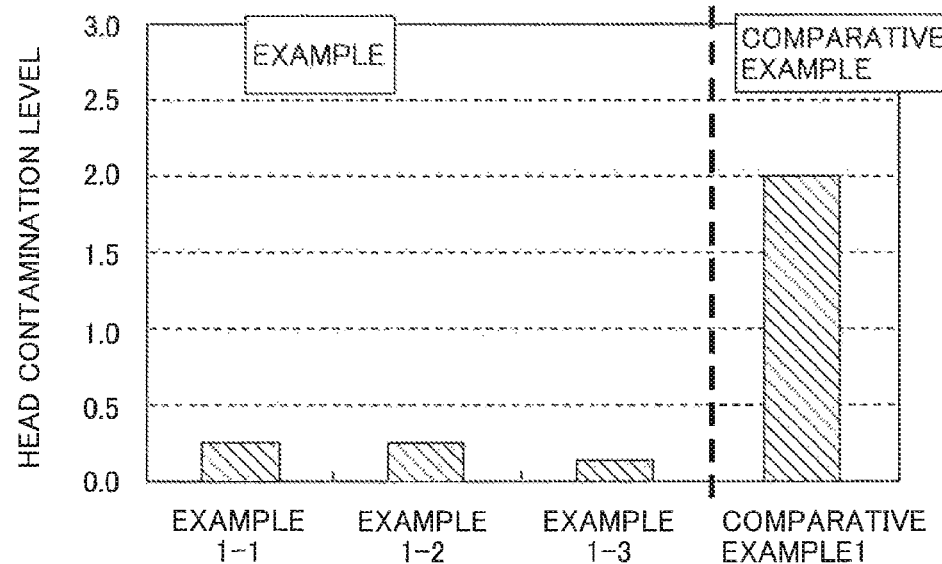
FIG. 1 is a graph illustrating a fixed-point floating test result after silicon exposure.

The present invention will be described below in detail by using an embodiment.

A lubricant compound for a magnetic disk of the present invention is, as described in the composition 1, a lubricant compound contained in a lubrication layer of a magnetic disk in which at least a magnetic layer, a protective layer, and the lubrication layer are sequentially provided on a substrate, and the lubricant compound contains a component A represented by Chemical formula 1 and a component B represented by Chemical formula 2:

$$X-\overset{H_2}{C}-\overset{F_2}{C}-O-\!\!\left(\overset{F_2}{C}-O\right)_{\!n}\!\!\left(\overset{F_2}{C}-\overset{F_2}{C}-O\right)_{\!m}\!\!\overset{F_2}{C}-\overset{H_2}{C}-X$$

wherein X in Chemical formula 1 represents OH $$X-\overset{H_2}{C}-\overset{F_2}{C}-O-\!\!\left(\overset{F_2}{C}-O\right)_{\!n}\!\!\left(\overset{F_2}{C}-\overset{F_2}{C}-O\right)_{\!m}\!\!\overset{F_2}{C}-\overset{H_2}{C}-X$$

wherein X in Chemical formula 2 represents $OCH_2CH(OH)CH_2OH$, and the lubricant compound further contains at least one type of a component C, wherein the component C is selected from compounds C-1, C-2 and C-3 represented by the following formulae:

(C-1)

$$HO\diagdown\diagup\diagdown_O\diagdown(Rf)-PN$$

(C-2)

$$HO\diagdown\diagup\diagdown_O\diagdown(Rf)-PN-(Rf)\diagdown_O\diagup\diagdown_{OH}^{OH}$$
$$HO$$

(C-3)

$$HOCH_2CF_2(Rf)OCF_2CH_2OCH_2CHCH_2O—*$$
$$\underset{OH}{|}$$
$$*—CH_2CHCH_2OCH_2CHCH_2OCH_2CF_2(Rf)OCF_2CH_2OH$$
$$\underset{OH}{|}\quad\underset{OH}{|}$$

wherein Rf represents —(OC$_2$F$_4$)m(OCF$_2$)n-, and m and n each represents an integer of not less than 1, and PN is represented from one of the following formulae:

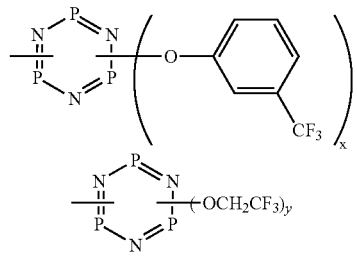

wherein x and y each is an integer of 5 when C is compound (C-1) and an integer of 4 when C is compound (C-2).

In the lubricant compound for a magnetic disk of the present invention, since the component D is not contained, aggregation or pickup of the lubricant hardly occurs, as compared with the FOMBLIN Z-TETRAOL (product name) lubricant, which has been used in general, and since the component C having an adsorption force to the protective film to the same degree as the component D, a function of reducing abrasion of the protective film or physical damage to the magnetic recording medium during LUL or in head contact is provided.

That is, since the prior-art component D has three hydroxyl groups for one terminal part, it can bind to the protective film extremely strongly, and thus, removal of the lubricant hardly occurs even in head contact, and abrasion of the protective film or physical damage to the magnetic recording medium can be reduced. However, since the positions of the hydroxyl groups in the molecule are close to the ends and they are close to each other in the component D, interactions such as hydrogen bonding can easily occur in the molecule or between the molecules, and aggregation of the lubricant can easily occur on the disk surface.

On the other hand, the component C contained in the lubricant of the present invention has fewer hydroxyl groups close to the end of the molecule than the component D, and aggregation between the molecules hardly occurs. Also, since it has a hydroxyl group not only at the end but also at the center part of the molecule as the compound C-3, the interaction between the molecules can be favorably suppressed. Also, by providing a phosphazene ring at the center part or end part of the molecule as a polar group (functional group) instead of the hydroxyl group as in the compounds C-1 and C-2, the interaction between the molecules can be favorably suppressed. Such component C can adsorb to the protective film not only at the end group but also at the center part of the molecule and has the adsorption force to the protective film equal to or larger than that of the component D, and thus, removal of the lubricant hardly occurs even in head contact, and abrasion of the protective film or physical damage to the magnetic recording medium can be reduced.

The lubricant compound for a magnetic disk of the present invention is a mixture of the component A, the component B, and the component C, and there is no particular need to restrict its mixing ratio in the present invention, but in order for the working effects by the present invention to exert better, the ratio of the component C is preferably 5 to 20 weight %. The component A and the component B can be also obtained by removing the component D from the commercially available FOMBLIN Z-TETRAOL (product name) lubricant, by appropriate refining, for example. Also, FOMBLIN Z-TETRAOL GT (product name) not containing the D component is also commercially available.

The content ratio between the components A and B is preferably anywhere between 1:3 and 1:10 (weight ratio).

Also, the component C is at least one type selected from the above compounds C-1, C-2, and C-3, but each compound may be used singularly or these compounds may be used at the same time as appropriate. Also, if these compounds are used at the same time, at least one type of the compounds C-1 and C-2 may be used at the same time with the compound C-3, for example. In the present invention, particularly the compounds C-2 and C-3 are preferable.

Each molecular weight of the component A, the component B, and the component C contained in the lubricant compound of the present invention is not particularly limited, but the number average molecular weight (Mn) is preferably within a range of 1000 to 10000, for example, and more preferably within a range of 1000 to 6000. That is because repairability by appropriate viscosity is provided, and favorable lubrication performances are exerted.

The lubricant compound of the present invention has the number average molecular weight (Mn) within a range of 1000 to 10000, for example, by an appropriate molecular weight fractionation. The method of molecular weight fractionation is not particularly limited in this case, and molecular weight fractionation using a gel permeation chromatography (GPC) method or molecular weight fractionation using a supercritical extraction method can be used, for example.

Also, the present invention is a magnetic disk in which at least a magnetic layer, a protective layer, and a lubrication layer are sequentially provided on a substrate, and the lubrication layer is also provided for the magnetic disk characterized by containing the lubricant compound for a magnetic disk of the present invention.

In forming the lubrication layer using the lubricant compound of the present invention, a film can be formed by application using a dip method, for example, using a solution in which the lubricant compound is dispersed and dissolved in a fluorine solvent or the like.

The film forming method of the lubrication layer is naturally not limited to the above dip method and a film forming method such as a spin coating method, a spraying method, a paper coating method and the like may be used.

In the present invention, in order to further improve an adhesion force of the formed lubrication layer to the protective layer, heating treatment or ultraviolet irradiation treatment may be conducted in which the magnetic disk is exposed to the atmosphere at 50 to 150° C. after the film formation.

The film thickness of the prior-art lubrication layer has been usually 15 to 18 Å, but in the present invention, the film thickness can be made thinner to the film thickness of approximately 10 to 13 Å, for example. If the thickness is less than 10 Å, lubrication performances as the lubrication layer might be lowered.

Also, as the protective layer in the present invention, a carbon protective layer can be favorably used. Particularly, an amorphous carbon protective layer is preferable. If the protective layer is a carbon protective layer, the interaction between the polar group (hydroxyl group or phosphazene ring) of the lubricant according to the present invention and the protective layer is further increased, and the working effect by the present invention is further exerted, which is a preferable mode.

In the carbon protective layer in the present invention, it is preferable that nitrogen is contained in the lubrication layer side of the protective layer so as to have a composition graded layer in which hydrogen is contained in the magnetic layer side, for example.

If the carbon protective layer is used in the present invention, a film can be formed by using a DC magnetron sputtering method, for example, but an amorphous carbon protective layer formed by the plasma CVD method is particularly preferable. By forming a film by the plasma CVD method, the surface of the protective layer is made uniform and closely formed. Therefore, formation of a lubrication layer according to the present invention on the protective layer formed by using the CVD method with smaller coarseness is preferable.

In the present invention, the film thickness of the protective layer is preferably 20 to 70 Å. If the thickness is less than 20 Å, performances as the protective layer might be lowered. The thickness exceeding 70 Å is not preferable from the viewpoint of film thinning.

In the magnetic disk of the present invention, the substrate is preferably a glass substrate. A glass substrate is rigid and is excellent in smoothness, which is preferable for higher recording density. As the glass substrate, an aluminosilicate glass substrate, for example, can be cited, and particularly a chemically-reinforced aluminosilicate glass substrate is preferable.

In the present invention, regarding coarseness of the main surface of the above substrate, the surface is preferably supersmooth with Rmax at 3 nm or less and Ra at 0.3 nm or less. The surface coarseness Rmax and Ra here are based on the specification by JIS B0601.

The magnetic disk obtained by the present invention is provided with at least a magnetic layer, a protective layer, and a lubrication layer on the substrate, but in the present invention, the magnetic layer is not particularly limited and may be either an in-plane recording type magnetic layer or a perpendicular recording type magnetic layer, but the perpendicular recording type magnetic layer is particularly preferable for realization of the recent rapid increase in recording density. Particularly, a CoPt magnetic layer is preferable since it can obtain both a high magnetic coercive force and a high reproduction output.

In the magnetic disk of the present invention, an underlayer can be provided between the substrate and the magnetic layer as necessary. Also, an adhesion layer or a soft magnetic layer or the like may be provided between the underlayer and the substrate. In this case, as the underlayer, a Cr layer, a Ta layer, a Ru layer or an alloy layer of CrMo, CoW, CrW, CrV, CrTi and the like can be cited, for example, and particularly the Ru layer is preferable in the perpendicular magnetic recording medium. As the adhesion layer, an alloy layer of CrTi, NiAl, AlRu and the like can be cited, for example. Also, as the soft magnetic layer, a CoZrTa alloy film, for example, can be cited.

According to the present invention, since the lubrication layer in which adhesion to the protective layer is high and aggregation or pickup of the lubricant, scratches and the like hardly occur can be formed, further reduction of the magnetic spacing can be realized, and moreover, under the circumstances of the super low floating amount (5 nm or less) of the magnetic head involved with the recent rapid increase in the recording density, a magnetic disk having high reliability under the extremely severe environmental resistance involved with diversification of applications can be obtained.

The magnetic disk of the present invention is preferable as a magnetic disk mounted particularly on an LUL-type magnetic disk device. A further decrease of the magnetic-head floating amount realized by introduction of the LUL method has required the magnetic disk to operate stably even with an extremely low floating amount of not more than 5 nm, for example, and the magnetic disk of the present invention having high reliability under the circumstance of the low floating amount is preferable.

EXAMPLES

The present invention will be described below in more detail by referring to examples.

Example 1

A magnetic disk of the present example has an adhesion layer, a soft magnetic layer, an under layer, a magnetic recording layer, a carbon protective layer, and a lubrication layer sequentially formed on a disk substrate.

(Manufacture of Magnetic Disk)

A 2.5-inch glass disk (outer diameter of 65 mm, inner diameter of 20 mm, and disk thickness of 0.635 mm) made of chemically reinforced aluminosilicate glass was prepared and used as a disk substrate. The main surface of the disk substrate was mirror-polished so as to have R max of 2.13 nm and Ra of 0.20 nm.

On this disk substrate, films of a Ti adhesion layer, a FeCoTaZr alloy thin-film soft magnetic layer, a NiW first underlayer, a RuCr second underlayer, and a $CoCrPtSiO_2$ alloy thin-film magnetic recording layer were formed sequentially in an Ar gas atmosphere by the DC magnetron sputtering method. This magnetic recording layer was a perpendicular magnetic recording type magnetic layer.

Subsequently, a film of an amorphous diamond-like carbon protective layer was formed with the film thickness of 60 Å by the plasma CVD method using a lower straight-chain hydrocarbon gas.

Subsequently, a lubrication layer was formed as follows. As the lubricant, a lubricant in which FOMBLIN Z-TETRAOL (product name) by Solvay Solexis, Inc. containing the component A and the component B (however, the component D is removed) and the compound C-2 (component C) (however, in the compound C-2, PN ring=$P_3N_3$ $(OC_6H_4CF_3)x$ (x=4)) are mixed at 9:1 (weight ratio) and adjusted as above was dispersed and dissolved with concentration of 0.2 weight % in VERTREL XF UP (product name) by DU PONT-MITSUI FLUOROCHEMICALS COMPANY, LTD., which is a fluorinated solvent, to prepare a solution.

By using this solution as an application liquid, the magnetic disk on which films were formed up to the protective layer was immersed and the liquid was applied by the dip method, and a film of the lubrication layer was formed.

After the film formation, the magnetic disk was subjected to heating treatment in a vacuum firing furnace at 100° C. for 60 minutes. The film thickness of the lubrication layer was measured by a Fourier transform infrared spectrophotometer (FTIR), and the result was 12 Å. A magnetic disk of Example 1-1 was obtained as above.

A magnetic disk of Example 1-2 fabricated similarly except that the film thickness of the lubrication layer was 14

Å and a magnetic disk of Example 1-3 fabricated similarly except that the film thickness of the lubrication layer was 16 Å were obtained.

Example 2

The lubrication layer was formed as follows.

As the lubricant, a lubricant in which FOMBLIN Z-TETRAOL (product name) by Solvay Solexis, Inc. containing the component A and the component B (however, the component D is removed) and the compound C-3 (component C) are mixed at 5:1 (weight ratio) and adjusted as above was dispersed and dissolved with concentration of 0.2 weight % in VERTREL XF UP (product name) by DU PONT-MITSUI FLUOROCHEMICALS COMPANY, LTD., to prepare a solution. The compound C-3 was manufactured by reacting 2 equivalent weight of the perfluoropolyether compound having a perfluoropolyether main chain in the molecule and having a hydroxyl group at the end with 1 equivalent weight of a diepoxy compound having a hydroxyl group in the molecule and an epoxide structure at the end.

By using this solution as an application liquid, the magnetic disk on which films were formed up to the protective layer was immersed and the liquid was applied by the dip method, and a film of the lubrication layer was formed. After the film formation, the magnetic disk was subjected to heating treatment in a vacuum firing furnace at 100° C. for 60 minutes. The film thickness of the lubrication layer was measured by a Fourier transform infrared spectrophotometer (FTIR), and the result was 14 Å.

A magnetic disk of Example 2 fabricated similarly to Example 1 except the lubrication layer was obtained.

Example 3

The magnetic disk of Example 3 was obtained similarly to Example 1 except that as the lubricant, a lubricant in which FOMBLIN Z-TETRAOL (product name) by Solvay Solexis, Inc. containing the component A and the component B (however, the component D is removed) and the compound C-2 (component C) (however, in the compound C-2, PN ring=$P_3N_3(OCH_2CF_3)y$ (y=4)) are mixed at 9:1 (weight ratio) and prepared was used. The film thickness of the lubrication layer was 14 Å.

Comparative Example 1

As the lubricant, a solution in which FOMBLIN Z-TETRAOL 2000S (product name) by Solvay Solexis, Inc. refined by the supercritical extraction method was dispersed and dissolved in VERTREL XF UP (product name) by DU PONT-MITSUI FLUOROCHEMICALS COMPANY, LTD. was used as an application liquid, the magnetic disk on which films were formed up to the protective layer was immersed therein and the liquid was applied by the dip method, and a film of the lubrication layer was formed. The film thickness of the lubrication layer was 14 Å. It was found that, as the result of NMR analysis, the lubricant has the component A at approximately 15%, the component B at approximately 70%, and the component D at approximately 15% (weight ratio).

A magnetic disk manufactured similarly to Example 1 except this point was obtained as Comparative Example 1.

Comparative Example 2

As the lubricant, a solution in which FOMBLIN Z-TETRAOL GT (product name) by Solvay Solexis, Inc. refined by the supercritical extraction method was dispersed and dissolved in VERTREL XF UP (product name) by DU PONT-MITSUI FLUOROCHEMICALS COMPANY, LTD. was used as an application liquid, the magnetic disk on which films were formed up to the protective layer was immersed therein and the liquid was applied by the dip method, and a film of the lubrication layer was formed. The film thickness of the lubrication layer was 14 Å. The concentration of the application liquid was adjusted, and those with the film thicknesses of the lubrication layer at 12 Å and 16 Å were also manufactured, respectively. It was found that, as the result of NMR analysis, the lubricant has the component A at approximately 85% and the component B at approximately 15% (weight ratio).

A magnetic disk manufactured similarly to Example 1 except this point was obtained as Comparative Example 2.

Figure 2:
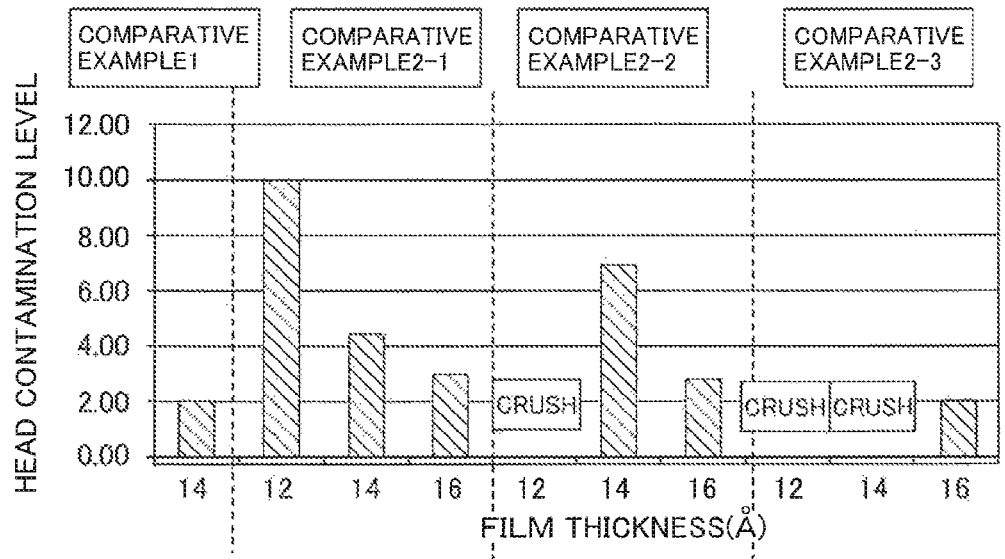
FIG. 2 is a graph illustrating a fixed-point floating test result after silicon exposure.

In FIG. 2, Comparative Examples 2-1 to 2-3 are illustrated and they indicate respective lots of the above tetraol GT.

Subsequently, the magnetic disks in Examples and Comparative Examples were evaluated by using the following test methods.

(Fixed-Point Floating Test)

After each magnetic disk is exposed to a silicon gas for 24 hours, a back-off amount was set to 1.5 nm by using DFH of magnetic head under a high-temperature condition at 75° C. and then, a fixed-point floating test at a position of 20 mm of the disk radius was conducted for continuous two hours. The result is shown in FIGS. 1 and 2. The results of Examples 2 and 3 are not illustrated in FIG. 1 but the result similar to Example 1 was obtained. Also, the magnetic disk manufactured similarly to Example 1 except that as the lubricant, the compound C-1 (however, in the compound C-1, PN ring=$P_3N_3(OC_6H_4CF_3)x$ (x=5)) was used instead of the compound C-2 was also evaluated similarly, and it was found that the head contamination level was approximately 1.0, which is poorer than Example 1.

In Examples 1, 2, and 3 and Comparative Example 1, a scratch was not observed in the medium but in Comparative Example 2, a crush failure occurred in the middle or a large number of scratches were observed in the medium.

Subsequently, regarding aggregation of the lubricant after the above fixed-point floating test, observation was made by using an optical surface analyzer (OSA). As a result, in Comparative Example 1, a large number of aggregated spots (Mogul spots) of 2000 or more were observed but in Examples 1, 2, and 3 and Comparative Example 2, the number of aggregated spots (Mogul spots) was 500 or less, which showed a favorable characteristic.

That is, the examples of the present invention show high abrasion properties represented by prevention of scratches and favorable characteristics in which the lubricant does not aggregate at the same time.

The invention claimed is:

1. A lubricant compound for a magnetic disk contained in a lubrication layer of a magnetic disk in which at least a magnetic layer, a protective layer, and a lubrication layer are sequentially provided on a substrate, characterized in that
the lubricant compound contains a component A represented by Chemical formula 1 and a component B represented by Chemical formula 2:

[Chemical formula 1]

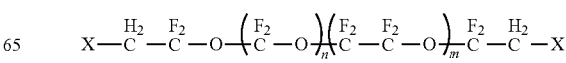

wherein X in Chemical formula 1 represents OH

[Chemical formula 2]

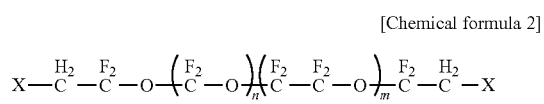

wherein X in Chemical formula 2 represents OCH$_2$CH(OH)CH$_2$OH,
and the lubricant compound further contains at least one type of a component C, wherein the component C is selected from compounds C-1 and C-2 represented by the following formulae:

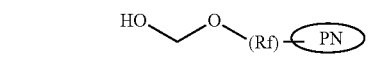

(C-1)

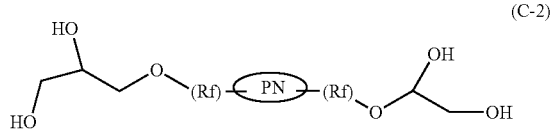

(C-2)

wherein Rf represents —(OC$_2$F$_4$)m(OCF$_2$)n-, and m and n each represents an integer of not less than 1, and PN is represented from one of the following formulae:

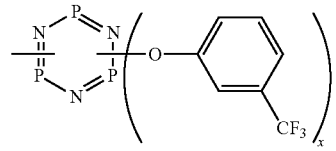

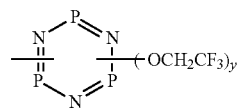

wherein x and y each is an integer of 5 when C is compound (C-1) and an integer of 4 when C is compound (C-2),
wherein the lubricant compound does not contain a component D represented by the following Chemical formula

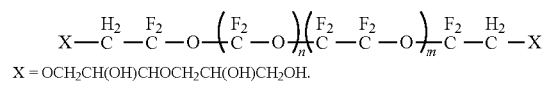

X = OCH$_2$CH(OH)CHOCH$_2$CH(OH)CH$_2$OH.

2. The lubricant compound for a magnetic disk according to claim 1, wherein in the lubricant compound, the ratio of the component C among the component A, the component B, and the component C is 5 to 20 weight %.

3. A magnetic disk in which at least a magnetic layer, a protective layer, and a lubrication layer are sequentially provided on a substrate, characterized in that
the lubrication layer contains the lubricant compound according to claim 1.

4. The magnetic disk according to claim 3, wherein the protective layer is a carbon protective layer formed by a plasma CVD method.

5. The magnetic disk according to claim 3, wherein the magnetic disk is mounted on a magnetic disk device whose start/stop mechanism is a load-unload type and used under the head floating amount of 5 nm or less.

6. The magnetic disk according to claim 3, wherein a thickness of the lubrication layer is 10 to 13 Å.

7. The lubricant compound for a magnetic disk according to claim 1, wherein a weight ratio between the components A and B is between 1:3 and 1:10.

* * * * *